US009498521B2

United States Patent
Johnson et al.

(10) Patent No.: US 9,498,521 B2
(45) Date of Patent: Nov. 22, 2016

(54) PURIFICATION, CHARACTERIZATION, AND USE OF CLOSTRIDIUM BOTULINUM NEUROTOXIN BONT/A3

(71) Applicant: Wisconsin Alumni Research Foundation, Madison, WI (US)

(72) Inventors: Eric Johnson, Madison, WI (US); William Tepp, Stoughton, WI (US); Guangyun Lin, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 1007 days.

(21) Appl. No.: 13/627,540

(22) Filed: Sep. 26, 2012

(65) Prior Publication Data

US 2015/0250861 A1    Sep. 10, 2015

Related U.S. Application Data

(60) Provisional application No. 61/540,321, filed on Sep. 28, 2011.

(51) Int. Cl.
| | |
|---|---|
| *A61K 38/48* | (2006.01) |
| *C07K 14/33* | (2006.01) |
| *C12N 9/52* | (2006.01) |

(52) U.S. Cl.
CPC ........... *A61K 38/4893* (2013.01); *C07K 14/33* (2013.01); *C12N 9/52* (2013.01); *C12Y 304/24069* (2013.01)

(58) Field of Classification Search
CPC .................................................. A61K 38/4893
See application file for complete search history.

(56) References Cited

U.S. PATENT DOCUMENTS

| | | | | |
|---|---|---|---|---|
| 5,512,547 A | * | 4/1996 | Johnson ............... | A61K 9/0019 514/15.2 |
| 9,125,804 B2 | * | 9/2015 | Webb .................. | A61K 9/0019 |

OTHER PUBLICATIONS

Arnon, et al., Botulinum Toxin as a Biological Weapon—Medical and Public Health Management, JAMA, 2001, 285(8):1059-1070.
Bihari, et al., Safety, Effectiveness and Duration of Effect of Botox After Switching from Dysport for Blepharospasm, Cervical Dystonia, and Hemifacial Spasm, Current Medical Research and Opinion, 2005, 21(3):433-438.
Carter, et al., Independent Evolution of Neurotoxin and Flagellar Genetic Loci in Proteolytic Clostridium Botulinum, BMC Genomics, 2009, 10:115, 18 pages.
Dover, et al., Novel Clostridium Botulinum Toxin Gene Arrangement with Subtype A5 and Partial Subtype B3 Botulinum Neurotoxin Genes, Journal of Clinical Microbiology, 2009, 47(7):2349-2350.
Iwasaki, et al., Acid Precipitation of Clostridium Botulinum Type C and D Toxins from Whole Culture by Addition of Ribonucleic Acid as a Precipitation Aid, Infection and Immunity, 1978, 19(2):749-751.
Jacobson, et al., Analysis of Neurotoxin Cluster Genes in Clostridium Botulinum Strains Producing Botulinum Neurotoxin Serotype A Subtypes, Applied and Environmental Microbiology, 2008, 74(9):2778-2786.
Jacobson, et al., Purification, Modeling, and Analysis of Botulinum Neurotoxin Subtype A5 (BoNT/A5) from Clostridium Botulinum Strain A661222, Applied and Environmental Microbiology, 2011, 77(12):4217-4222.
Johnson, Clostridial Neurotoxins, Chapter 21, Handbook on Clostridia, 2005, Edited by P. Durre, CRC Press, Inc., Boca Raton, FL, pp. 491-525.
Marshall, et al., Plasmid Encoded Neurotoxin Genes in Clostridium Botulinum Serotype A Subtypes, Biochem. Biophys. Res. Commun., 2007, 361(1):49-54.
Matsuda, et al., Rapid Method for Purification of Clostridium Botulinum Type C Neurotoxin by High Performance Liquid Chromatography (HPLC), European Journal of Epidemiology, 1986, 2(4):265-271.
Mazuet, et al., Characterization of Botulinum Neurotoxin Type A Neutralizing Monoclonal Antibodies and Influence of Their Half-Lives on Therapeutic Activity, PLoS One, 2010, 5(8):e12416, 11 pages.
Miyazaki, et al., Clostridium Botulinum Type D Toxin: Purification, Molecular Structure, and Some Immunological Properties, Infection and Immunity, 1977, 17(2):395-401.
Reed, et al., A Simple Method of Estimating Fifty Per Cent Endpoints, The American Journal of Hygiene, 1938, 27(3):493-497.
Smith, G., et al., A Comparison of the Distribution of Clostridium Botulinum in Soil and in Lake Mud, J. Hyg., Camb., 1977, 78:39-41.
Smith, T., et al., Analysis of the Neurotoxin Complex Genes in Clostridium Botulinum A1-A4 and B1 Strains: BoNT/A3, /Ba4 and /B1 Clusters Are Located Within Plasmids, PLoS One, 2007, 2(12):e1271, 10 pages.
Markus, Botox for Wrinkles, Baylor College of Medicine, http://www.bcm.edu/dermatology/?PMID=1909, initially accessed Sep. 30, 2009.

\* cited by examiner

*Primary Examiner* — Kara Johnson
(74) *Attorney, Agent, or Firm* — Quarles & Brady LLP

(57) ABSTRACT

Preparations of *Clostridium botulinum* neurotoxin BoNT/A3 and methods for using such preparations for treating a patient having a symptom in need of botulinum toxin therapy are provided herein.

4 Claims, 2 Drawing Sheets

ABSTRACT

PURIFICATION, CHARACTERIZATION, AND USE OF CLOSTRIDIUM BOTULINUM NEUROTOXIN BONT/A3

CROSS-REFERENCE TO RELATED APPLICATIONS

This application claims the benefit of U.S. Provisional Application No. 61/540,321, filed on Sep. 28, 2011, which is incorporated herein by reference in its entirety.

STATEMENT REGARDING FEDERALLY SPONSORED RESEARCH OR DEVELOPMENT

This invention was made with government support under AI065359 and AI057153 awarded by the National Institutes of Health. The government has certain rights in the invention.

FIELD OF THE INVENTION

The present invention relates to preparations of *Clostridium botulinum* neurotoxin BoNT/A3 and methods for using such preparations for treating a patient having a symptom in need of botulinum toxin therapy.

BACKGROUND OF THE INVENTION

*Clostridium botulinum* produces a characteristic botulinum neurotoxin (BoNT), which is classified by the Centers for Disease Control and Prevention as one of the six highest-risk threat agents for bioterrorism ("Category A" bioterrorism agents). BoNT is a 150 kDa single chain protein which is linked by a disulfide bond which can be cleaved into a 100 kDa Heavy Chain (HC) and a 50 kDa Light chain (LC) by endogenous or exogenous proteases. The LC is a zinc metalloprotease which cleaves different SNARE proteins depending on the serotype causing flaccid paralysis. The HC consists of a C-terminal binding domain ($H_C$) which is responsible for receptor binding and a N-terminal translocation domain ($H_N$) which is responsible for delivering the catalytic light chain to the neuronal cytosol. Based on their ability to be neutralized by type specific antiserum, BoNTs have traditionally been categorized into seven serotypes (BoNT/A-G), among which BoNTs A, B, E and F are known to cause human botulism. *Clostridium botulinum* type A (BoNT/A) is of particular importance and interest due to its implication in human botulism cases, and its potential for use as a bioterrorism agent. It is also the serotype most commonly used in the medical field to treat muscle movement disorders and in the cosmetic industry to smooth facial wrinkles bringing large profits to the pharmaceutical industry.

There are currently five different type A subtypes identified as A1, A2, A3, A4 and A5 (Carter et al., *BMC Genomics* 10:115 (2009); Dover et al., *J. Clin. Microbiol.* 47(7):2349-2350 (2009); Jacobson et al., *Appl. Environ. Microbiol.* 77(12):4217-4222 (2011)). BoNT/A1 is the most studied and commonly used for the clinical purposes. BoNT/A1 and BoNT/A5 are very similar: both containing a HA neurotoxin gene cluster, while BoNT/A2, BoNT/A3 and BoNT/A4 contain an OrfX neurotoxin gene cluster (Jacobson et al., *Appl. Environ. Microbiol.* 74:2778-2786 (2008); Jacobson et al., *Appl. Environ. Microbiol.* 77(12):4217-4222 (2011)). Both bont/A3 and bont/A4 are located on a plasmid instead of a chromosome (Marshall et al., *Biochem. Biophys. Res. Commun.* 361:49-54 (2007); Smith et al., *PLoS ONE* 2(12): e1271 (2007)). Interestingly, BoNT/A3 could not be effectively neutralized by anti-BoNT/A1 antibody, which is the only serum currently available to treat botulism (Mazuet et al., *PLoS One* 5(8):e12416 (2010)).

While BoNT/A3 has interesting properties, purification of BoNT/A3 is challenging due to its low levels of production. It would be advantageous, therefore, to develop improved methods for obtaining highly pure preparations of BoNT/A3.

SUMMARY OF THE INVENTION

In one aspect, the present invention provides a preparation of *Clostridium botulinum* neurotoxin BoNT/A3. The preparation can be at least 90% pure toxin complex. The specific toxicity can be at least $5 \times 10^7$ $LD_{50}$ per m/g.

In another aspect, the present invention provides a preparation of *Clostridium botulinum* neurotoxin. The preparation can be at least 90% pure BoNT/A3. The specific toxicity can be at least $5 \times 10^7$ $LD_{50}$ per m/g.

In a further aspect, the present invention provides a method of treating a patient having a symptom in need of botulinum toxin therapy. The method comprises treating the patient with an effective amount of a preparation of *Clostridium botulinum* neurotoxin BoNT/A3 whereby the symptom is reduced. The preparation can be at least 90% pure toxin complex. The preparation can be at least 90% pure BoNT/A3. The specific toxicity can be at least $5 \times 10^7$ $LD_{50}$ per m/g. The treatment can be for a condition selected from the group consisting of cervical dystonia, blepharospasm, severe primary axillary hyperhidrosis, strabismus, achalasia, chronic focal neuropathies and migraine and other headache disorders, cosmetic issues, muscle spasms, upper motor neuron syndrome, sweating, and neurological disorders treated with BoNT/A1.

DESCRIPTION OF THE INVENTION

In general

Figure 1:
FIG. 1 presents an image showing acid precipitation in cultures with (right bottle) and without (left bottle) RNA. Arrows indicate the visible precipitation.

In its most general aspect, the present invention encompasses a preparation of *Clostridium botulinum* neurotoxin BoNT/A3.

Botulinum neurotoxins have traditionally been characterized into seven serotypes (BoNTs/A-G). The serotype BoNT/A1 is important because it causes the most severe botulism toxicity and is commonly used in the pharmaceutical industry. Subtype A3 is commercially interesting because BoNT/A3 is not effectively neutralized by anti-BoNT/A1 antibodies. This immunological difference suggests that BoNT/A3 is a candidate to potentially replace BoNT/A1 for patients who have developed neutralizing antibodies to BoNT/A1 due to repeated treatments or immunization.

Preparations of the Present Invention

In one embodiment, the present invention is an isolated preparation of *Clostridium botulinum* neurotoxin BoNT/A3 wherein the preparation is at least 90% neurotoxin. In another embodiment, the preparation is at least 90%, preferably 95%, pure BoNT/A3 or BoNT/A3 complex. In another embodiment, the preparation is a crude culture extract wherein the toxicity is at least $9 \times 10^3$ $LD_{50}$ per ml.

Methods of the Present Invention

The present invention provides a method for purifying the ~150 kDa BoNT/A3. In one embodiment, the present invention is a purification method that produces a greater than 90%, preferably 95%, pure BoNT/A3 preparation.

In one embodiment, one would begin by inoculating a "CDC" or "Loch Maree A3 strain" into modified Mueller-Miller medium. One may obtain CDC A3 from the Center for Disease Control in Atlanta, Ga. We believe the Loch Maree A3 strain to be substitutable.

Modified Mueller-Miller medium is described below in Table 1 and in Example 1.

Typically, after inoculation with an actively growing culture, the modified Mueller-Miller medium is incubated statically for 5 days for 37° C. and then cooled down on ice. Preferably, at least 0.3 g RNA (0.2 g/L) is added and pH adjusted to 3.5. As described in Example 2 below, the addition of RNA can be useful in enhancing precipitation. See Miyzaki et al., *Infection and Immunity* 17(2):395-401 (1977); Iwasaki et al., *Infection and Immunity* 19(2):749-751 (1978). One may wish to substitute another polynucleotide or modify RNA concentration.

After precipitation, the pellet is extracted twice in a citrate buffer and supernatants, 60% saturated with ammonium sulfate, were stored at 4° C.

Ammonium sulfate precipitate is collected from the first extraction and resuspended in $NaPO_4$ buffer pH 6.0. Ribonuclease A and then trypsin are added. The treated solution is precipitated and then subjected to chromatography steps as described in Example 1 below.

Table 2 describes a typical recovery percentage of the method of the present invention. Note that the crude culture has a toxicity of at least $9.2 \times 10^3$ $LD_{50}$ per m/L. After chromatography, the present invention provides a preparation of at least 90%, preferably 95%, pure toxin complex (TC), which contains BoNT/A3 and nontoxin-nonhemagglutinin NTNH. The ~95% pure toxin complex is obtained after the CM chromatographic step. 95% purity means that only approximately 5% of the proteins seen on SDS-PAGE are proteins other than the toxin or NTNH. A preparation of at least 90%, preferably 95%, pure BoNT/A3 is provided after Mono-Q chromatography eluting at a salt concentration of approximately 150 mM.

Toxicity testing demonstrates that a typical specific toxicity of the 150 kDa protein is approximately $5.8 \times 10^7$ $LD_{50}$/mg. In a preferred embodiment, the specific activity is at least $5.0 \times 10^7$ $LD_{50}$/mg. This toxicity is significant because it is close to the specific toxicity of BoNT/A1, purified in our laboratory, which was approximately $1 \times 10^8$ $LD_{50}$/mg.

It is noteworthy that the data presented herein demonstrate that mice injected with a dose of the BoNT/A3 preparation showed initial botulism symptoms. Preliminarily, these symptoms seem different than those of similar mice injected with BoNT/A1, possibly suggesting that BoNT/A3 affects neurons by a different metabolic pathway. Neutralization results showed that anti-BoNT/A1 antibody was able to fully neutralize 10,000 $LD_{50}$ of BoNT/A1. The same amount of BoNT/A1 could only neutralize 1,000 $LD_{50}$ of BoNT/A3 and could not neutralize 2,500 $LD_{50}$ of BoNT/A3. This data indicates that may be important differences in epitopes between BoNT/A1 and BoNT/A3 that lead to differences in neutralizing antibody formation in immunized animals.

TABLE 1

| Mueller & Miller Medium | |
|---|---|
| Modified Mueller & Miller Medium | Mueller & Miller Medium |
| NZ Case TT (20 g/1 L), | Casein solution |
| $Na_2$ $HPO_4$ (1 g/1 L), | $Na_2$ $HPO_4$ (1 g/1 L), |
| $KH_2PO_4$ (0.15 g/L), | $KH_2PO_4$ (0.15 g/L), |
| $MgSO_4 \cdot 7H_2O$ (0.15 g/L), | $MgSO_4 \cdot 7H_2O$ (0.15 g/L), |
| $FeSO_4 \cdot 7H_2O$ (1% solution, 0.04 g/L), | $FeSO_4 \cdot 7H_2O$ (1% solution, 0.04 g/L), |
| Cysteine HCl (0.25 g/L), | Cysteine HCl (10%), |
| beef heart infusion (0.5 ml/L), (Difco beef heart for infusion), | beef heart infusion (0.05 ml/L), (fresh beef heart), |
| Glucose (10 g/L). | Glucose (11 g/L). |
| NO | NaCl 2.5 g |
| NO | Tyrosine-HCl (10%) |
| NO | Uracil-HCl (2.5%) |
| NO | Ca-pantothenate in ethanol (25%) |
| NO | Thiamine in ethanol (25%) |
| NO | Pyridoxine-HCl in ethanol (25%) |
| NO | Riboflavin in ethanol (25%) |
| NO | Biotin in ethanol (25%) |
| NO | |
| pH 7.3 | pH 7.3 |

In another embodiment, the present invention is drawn to a method of treating a patient in need of botulinum therapy. As used herein, the term "treating" refers to reducing, eliminating, improving the condition of, or lessening the severity of any aspect of a symptom in need of botulinum toxin therapy in a patient. In particular, the present invention includes a method of treating a patient having a symptom in need of botulinum toxin therapy. In such cases, the method can comprise treating the patient with an effective amount of a BoNT/A3 preparation provided herein whereby the symptom is reduced.

A BoNT/A3 preparation of the present invention can be administered in a therapeutically effective amount within a wide dosage range. Methods of determining a suitable dosage or dosage range for individual treatments are known to those in the art. For the methods provided herein, a BoNT/A3 preparation of the present invention can be administered by any means that achieves the intended purpose or is deemed appropriate by those of skill in the art. In an exemplary embodiment, a BoNT/A3 preparation is administered either as a single dose or, where appropriate, as continuous administration using, for instance, a mini pump system. In some cases, a BoNT/A3 preparation is provided as a liquid dosage form or as a lyophilized dosage form that is, for example, reconstituted prior to administration.

It is contemplated that the BoNT/A3 preparations of the present invention can be substituted for one or more BoNT/A1 therapeutics. For example, one may wish to treat blepharospasm, strabismus, cosmetic issues (e.g., eye wrinkles and "crows feet"), muscle spasms, upper motor neuron syndrome, sweating, cervical dystonia, chronic migraine, and other indications currently treated with BoNT/

A1 with one or more of the BoNT/A3 preparations of the present invention. The data presented herein suggest that BoNT/A3 can replace BoNT/A1 for those people who have developed an antibody against BoNT/A1.

In an exemplary embodiment, the methods provided herein can be practiced for a subject who produces neutralizing antibodies directed against BoNT/A1. For example, a subject may produce neutralizing antibodies directed against BoNT/A1 during or following treatment of a symptom in need of botulinum toxin therapy. Such treatment can comprise administration of pure BoNT/A1 neurotoxin or pure BoNT/A1 neurotoxin complex.

The methods provided herein can be practiced in prior to, after, or concurrently with any other therapy. For example, the methods described herein can be performed for a subject receiving on-going treatment for an unrelated condition.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

Various exemplary embodiments of compositions and methods according to this invention are now described in the following examples. The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Materials and Methods for Purifying BoNT/A3

Medium, strain and purification materials: CDC A3 strain was inoculated into Modified Mueller-Miller medium (Mueller et al., *J. Clin. Invest.* 22:315-318 (1943)): NZ Case TT (20 g/1 L), $Na_2HPO_4$ (1 g/1 L), $KH_2PO_4$ (0.15 g/L), $MgSO_4 \cdot 7H_2O$ (0.15 g/L), $FeSO_4 \cdot 7H_2O$ (1% solution, 0.04 g/L), Cysteine HCl (0.25 g/L), beef heart infusion (0.5 ml/L), Glucose (10 g/L). The medium pH was adjusted to 7.3 using NaOH. NZ Case TT was purchased from Kerry Bioscience. Beef heart infusion was purchased from Difco. Soy Bean Trypsin inhibitor (SBIT), RNA, RNaseA, DEAE-Sephadex A-50, CM-Sepharose (CL-6B) and all other medium components were purchased from Sigma. Mono Q (HR5/5) was purchased from Pfizer-Phamacia Inc. Trypsin was purchased from Worthington, 4-12% Bis-Tris SDS-PAGE gels and SeeBlue Plus 2 Pre-Stained protein marker were purchased from Invitrogen.

Extraction of crude A3 neurotoxin from the culture with or without adding RNA: Two bottles of 1.5 liter (L) sterile Modified Mueller-Miller medium were inoculated with 1.5 ml of actively growing CDC A3 culture (24 hr) and incubated statically for 5 days at 37° C. The 5 day culture was cooled down for 60 minutes on ice, and 0.3 g RNA (0.2 g/L) was added to one of two bottles containing the 1.5 L A3 culture to determine if RNA will help to precipitate the toxin more efficiently. The pH of the culture in both bottles was then adjusted to 3.5 using 3 N $H_2SO_4$ and allowed to stand at room temperature for 1 hour. The difference in the amount of settled precipitate between the two bottles with or without adding RNA was visually observed and then confirmed by a toxicity testing. The acid precipitate was collected by centrifugation and washed with a total of 200 ml distilled water. The pellet was extracted twice by gentle stirring for 2 hours at room temperature in 200 ml 0.1M NaCitrate buffer pH 5.5 containing 200 μl aprotinin. The extracts were centrifuged and the supernatants which were 60% saturated with ammonium sulfate were stored at 4° C. Sample aliquots from the whole culture, supernatant after acid precipitation and extract supernatant were saved for toxicity testing.

Comparison of toxin recovery between the cultures with and without adding RNA before acid precipitation: Toxin recovery percentage was compared via toxicity testing. Samples which included A3 crude culture, supernatants after acid precipitation from the culture either with or without adding RNA, and extract supernatants were collected. Toxicity was determined by IV injection of the nicked (trypsinized) or un-nicked samples into groups of mice. Each mouse was injected with 100 μl sample diluted 1:1 in gelatin phosphate buffer (30 mM NaPhosphate pH 6.3+0.2% gelatin) and 4 mice were used per group. IV time to death was converted to IP $LD_{50}$/ml by comparison to a standard type A1 curve developed in our laboratory.

Purification of BoNT/A3: 100 ml of ammonium sulfate precipitate from the first extraction was collected by centrifugation and resuspended in 20 ml 50 mM $NaPO_4$ buffer pH 6.0. Ribonuclease A (RNAse A) was added at the final concentration of 100 μg/ml and incubated for 3 hours at 37° C. The solution after digestion was centrifuged to remove insoluble material. Trypsin was then added to the solution to a final concentration of 100 μg/ml and was incubated for 30 minutes at 37° C. to nick remaining single chain toxin. Soybean Trypsin Inhibitor (SBTI) was added to the solution to a final concentration of 200 μg/ml and incubated for 10 minutes at room temperature to inactivate trypsin. The treated solution was precipitated with solid ammonium sulfate (39 g/100 ml) and stored at 4° C. To obtain purified BoNT/A3, the following chromatography steps were used:

DEAE Chromatography pH 5.5: The RNAse A and trypsin treated ammonium sulfate precipitated pellet was collected by centrifugation, resuspended in 1 ml of 0.05 M NaCitrate pH 5.5, and dialyzed for 4 hours at room temperature with 3 dialysis changes at one hour intervals. The dialyzed solution was centrifuged to remove insoluble material and the supernatant was loaded on a 8 ml (0.9 cm×13 cm) DEAE Sephadex A-50 column equilibrated with 50 mM NaCitrate buffer pH 5.5 at room temperature. The column was washed with 50 mM NaCitrate buffer pH 5.5. The unbound fractions were collected directly, and the bound proteins were eluted with 0.05 M NaCitrate pH 5.5 buffer containing 0.8 M NaCl. Fractions were monitored at $OD_{278}$ and analyzed by SDS-PAGE. The unbound fractions containing the crude toxin complex were pooled as unbound pool 1 ($A_{260}/A_{278}$ ratio less than 0.6) and unbound pool 2 ($A_{260}/A_{278}$ ratio greater than 0.6) and precipitated with solid ammonium sulfate (39 g/100 ml) and stored at 4° C.

CM Sepharose chromatography: The ammonium sulfate precipitated crude toxin complex from the DEAE pH 5.5 column was collected by centrifugation and resuspended in 1 ml 0.025 M sodium citrate buffer, pH 6.0. The solution was dialyzed at room temperature with 3 dialysis changes at one hour intervals and loaded on a 0.9 cm×12 cm CM sepharose column. The column was washed with 25 mM NaCitrate buffer, pH 6.0. The unbound fractions were collected directly, and the bound proteins were eluted with 0.025 M sodium citrate buffer, pH 6.0 containing 0.5 M NaCl. The fractions were monitored at $OD_{278}$ and analyzed by SDS-PAGE. The fractions containing ~95% pure toxin complex (TC) were pooled as unbound pool 1 ($A_{260}/A_{278}$ ratio less than 0.6) and unbound pool 2 ($A_{260}/A_{278}$ ratio greater than 0.6) and precipitated by addition of ammonium sulfate (39 g/100 ml).

FPLC mono-Q chromatography: The precipitated toxin complex from the CM sepharose chromatography was collected by centrifugation, resuspended in 4 ml 20 mM sodium phosphate buffer pH 8.0, and dialyzed at room temperature with 3 dialysis changes at one hour intervals. The dialyzed solution was loaded on a FPLC Mono-Q column (1 ml/min) for separation of the toxin from NTNH. A NaCl gradient from 0 to 0.35 M was applied to the column to elute the bound material. The fractions were monitored at $OD_{278}$ and analyzed by SDS-PAGE. Data showed that the A3 toxin, along with several minor contaminating proteins, was recovered in the first peak at 147 mM NaCl. Those fractions were pooled and precipitated with ammonium sulfate. Purity was determined by densitometry of a 4-12% SDS-PAGE gel.

Specific toxicity determination: The specific toxicity of the purified 150 kDa BoNT/A3 was determined by IP injection of the following 5 different toxin amounts into groups of mice (4 mice/group): 25 pg, 20 pg, 15 pg, 10 pg, 5 pg/mouse. The toxin was diluted in 0.5 ml gelatin phosphate buffer and injected IP. The injected mice were observed for 4 days. The $LD_{50}$/mg of toxin was calculated using the method of Reed and Muench (*Am. J. Hygiene* 27:493-497, 1938).

Observation of botulism symptoms in the mice IV injected with BoNT/A3: Two groups of mice (4 mice/group) were IV injected BoNT/A3 at dose of ~$5 \times 10^5$ $LD_{50}$/ml or $1 \times 10^5$ $LD_{50}$/ml, respectively. Mice were observed for symptoms of botulism from the time of injection until the time of death.

Neutralization of BoNT/A3 using anti-BoNT/A1 antibody: Serum from rabbits immunized with BoNT/A1 toxoid was fractionated by Protein A chromatography to obtain polyclonal anti-BoNT/A1 IgG. One microliter of the purified antibody was able to neutralize ~5,000 $LD_{50}$ of BoNT/A1. In this study, 2 pl of antibody was mixed with 15,000 $LD_{50}$, 10,000 $LD_{50}$ and 5,000 $LD_{50}$ of BoNT/A1 or 15,000 $LD_{50}$, 10,000 $LD_{50}$, 5,000 $LD_{50}$, 2,500 $LD_{50}$, 1,000 $LD_{50}$ and 100 $LD_{50}$ of BoNT/A3 respectively to compare the ability of the anti-BoNT/A1 antibody to neutralize either BoNT/A1 or BoNT/A3. Toxin was diluted with gelatin phosphate to achieve the appropriate $LD_{50}$ concentrations. The different mixtures of toxin and antibody were incubated at 37° C. for 90 minutes prior to injection. Each mouse within the group (4 mice) was injected with 0.5 ml of the toxin+antibody mixture and observed for 4 days for symptoms.

Miller medium was used and the toxin production level increased at least 10 fold using the new medium (data not shown).

Comparison of toxin recovery between the cultures with and without adding RNA before acid precipitation: Precipitation differences were visible after adding RNA to the culture (FIG. 1). The size of the pellet collected from the culture with the RNA added was larger than that from the culture without the RNA added. IV injection was performed as described in the Materials and Methods part. Table 2 presents recovery percentage, specific toxicity, and total toxicity calculations. As shown in Table 2, only 2.9% of toxin was left in the supernatant after adding RNA, while 17.8% of toxin was still left in the supernatant without adding RNA to the culture before acid precipitation. Data also indicated that RNA plays an important role in increasing the toxin precipitation percentage, and that approximately 100% of toxin was recovered from the first extraction and trypsinized (nicked) toxin had an approximately 2 fold higher specific toxicity than non-trypsinized toxin. Note that the crude culture has a toxicity of at approximately $9.2 \times 10^3$ $LD_{50}$ per m/L. After chromatography, the present invention provides a preparation of at least 90%, preferably 95%, pure toxin complex (TC), which contains BoNT/A3 and non-toxin-nonhemagglutinin NTNH. The ~95% pure toxin complex is obtained after the CM chromatographic step. 95% purity means that only approximately 5% of the proteins seen on SDS-PAGE are proteins other than the toxin or NTNH. A preparation of at least 90%, preferably 95%, pure BoNT/A3 is provided after Mono-Q chromatography eluting at a salt concentration of approximately 150 mM.

When the commonly used isolation/precipitation method (i.e., acid alone) is used to isolate BoNT/A1 neurotoxin, approximately 90% of BoNT/A1 neurotoxin is recovered. By comparison, the RNA-addition method described herein recovered nearly 100% BoNT/A3 neurotoxin based on the mouse bioassay (Table 2). This level of neurotoxin recovery is not common, but variation inherent to the mouse toxicity bioassay must be taken into account.

Type A botulinum neurotoxin usually does not require trypsinization and no such enzymatic treatment is performed in the production of commercial type BoNT/A1 neurotoxin. Our data identifies another unique property distinguishing BoNT/A3 neurotoxin from BoNT/A1 neurotoxin, namely that trypsinization of BoNT/A3 neurotoxin results in a 2-fold increase in its specific toxicity.

TABLE 2

Recovery percentage comparison between the culture with and without adding RNA before acid precipitation

|  | Avg. minutes to death (min) | Toxicity ($LD_{50}$/ml) | Total toxicity | Recovery Percentage (%) |
| --- | --- | --- | --- | --- |
| A3 Culture | 118.31 | $9.19 \times 10^3$ | $5.51 \times 10^7$ |  |
| Acid Supernatant without adding RNA | 124.13 | $6.57 \times 10^3$ | $9.85 \times 10^6$ | 17.8% of starting toxicity |
| Acid Supernatant with adding RNA | 155.88 | $1.056 \times 10^3$ | $1.58 \times 10^6$ | 2.9% of starting toxicity |
| A3 Extract 1 Unnicked | 80.5 | $8.1 \times 10^4$ | $6.318 \times 10^7$ | 100% |
| A3 Extract 1 Nicked | 68.31 | $1.63 \times 10^5$ | $1.271 \times 10^8$ | 100% |

Example 2

Results from BoNT/A3 Purification

Figure 2:
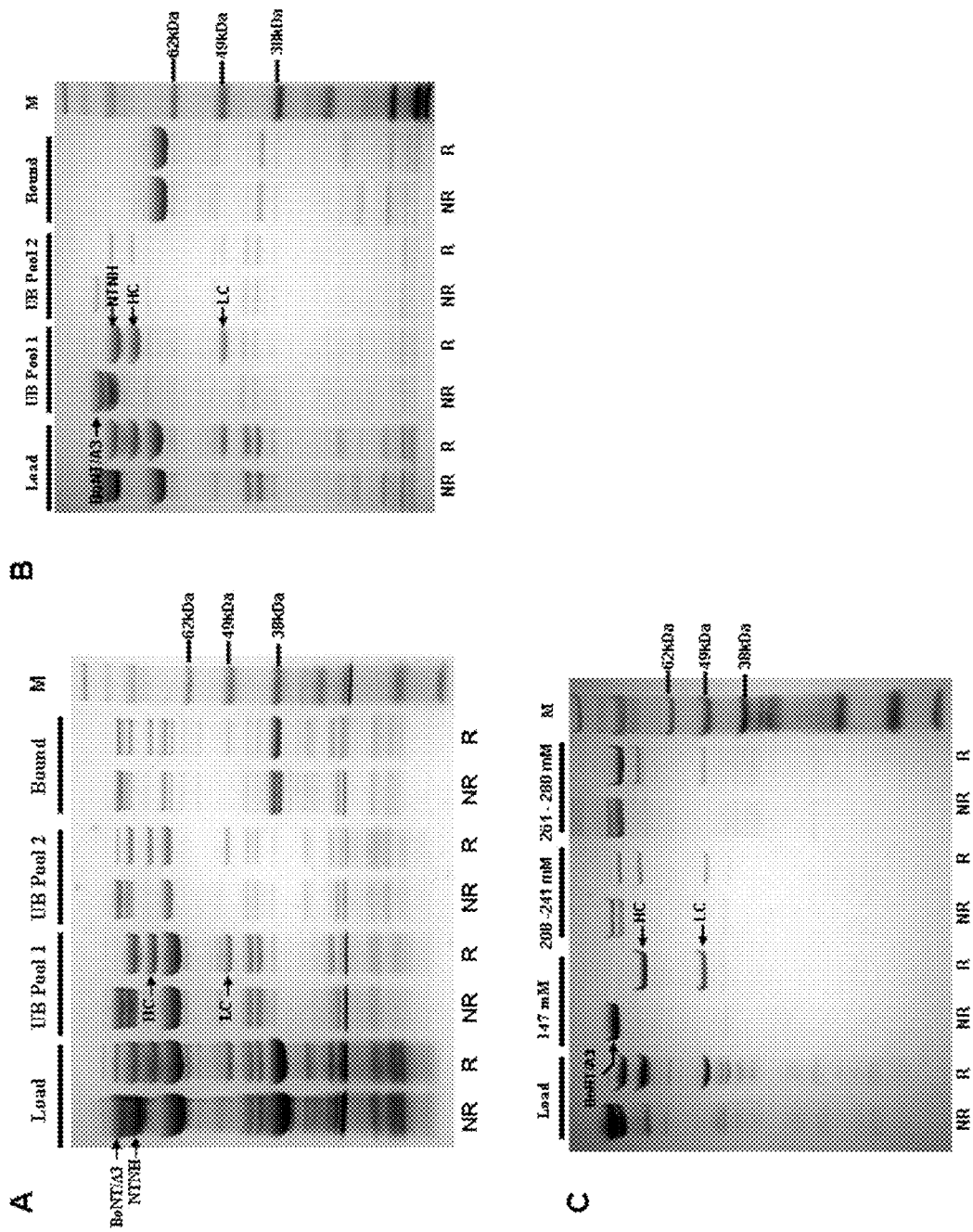
FIG. 2 presents images of Coomassie blue stained SDS-PAGE gels under non-reducing and reducing conditions. A. Coomassie blue stained SDS-PAGE gel analysis of fractions after DEAE-Sephadex A-50 chromatography. Data showed BoNT/A3 complex with $A_{260}/A_{278}$ ratio less than 0.6 in unbound fractions pool 1. B. Coomassie blue stained SDS-PAGE gel analysis of fractions after CM-Sepharose chromatography. Data showed that 95% pure BoNT/A3 complex was obtained in unbound fractions pool 1. C. Coomassie blue stained SDS-PAGE gel analysis of fractions after Mono-Q chromatography. Data showed that 95% pure BoNT/A3 was obtained in the fraction at 147 mM salt concentration. UB: Unbound, NR: Non-reduced, R: Reduced, HC: Heavy chain, LC: Light chain, M: Marker.

Modified Mueller-Miller medium increased the production level of BoNT/A3: In this study, a Modified Mueller- Purification of BoNT/A3: After obtaining crude BoNT/A3 extract from the culture, three chromatography steps were used to purify BoNT/A3. First, the crude toxin extract was chromatographed on a DEAE-Sephedex A-50 column. Nucleic acid and a major protein band of ~38 kDa were removed from the crude toxin extract (FIG. 2A). The majority of BoNT/A3 complex remains in the fractions from the first unbound peak. Pool 1 containing the toxin complex was further purified by chromatography on a CM Sepharose column. The unbound fractions in pool 1 from the CM chromatographic step yielded 95% pure toxin complex (TC) containing BoNT/A3 and NTNH with a $A_{260}/A_{278}$ ratio less than 0.6 (FIG. 2B). BoNT/A3 was then separated from NTNH using FPLC Mono Q chromatography. A 95% pure BoNT/A3 was eluted at salt concentration of 147 mM (FIG. 2C). The purified 150 kDa toxin was confirmed by SDS-PAGE under both unreduced and reduced conditions and by mouse bioassay. Approximately 210 μg of pure BoNT/A3 was obtained at this final step; therefore, a total of 420 μg of pure BoNT/A3 was expected to be obtained from the 1.5 L starting culture because only half of the extract was used in the toxin purification. Based on the toxicity results from the starting culture and final product, the recovery of toxicity was approximately between 21-42%, which is similar to that of BoNT/A1.

BoNT/A3 toxicity testing: The toxicity of BoNT/A3 was determined by IP injection as described in Materials and Methods. Specific toxicity of the 150 kDa protein was determined to be ~$5.76\times10^7$ $LD_{50}$/mg. It is close to the specific toxicity of BoNT/A1 that was purified in our laboratory, which is ~$1\times10^8$ $LD_{50}$/mg.

Observation of botulism symptoms in the mice IV injected with BoNT/A3. The mice injected IV with a dose of $5\times10^5$ $LD_{50}$ of BoNT/A3 started to show initial botulism symptoms approximately 35-40 minutes after the injection. Paralysis started with the front legs, spread to the whole body, and then mice died (on average) approximately 68 minutes after injection. No symptoms like ruffled fur or wasped abdomen that usually applies to BoNT/A1 were observed (Table 3).

TABLE 3

Botulinum Symptoms Differences in the Mice IV Injected with BoNT/A3

| C. botulinum symptoms | A1 | A3 |
| --- | --- | --- |
| Ruffled Fur | Yes | No |
| Wasped abdomen | Yes | No |
| Jumping around before die | Yes | No |
| Front leg paralysis | No | Yes |
| Hind leg paralysis | No | Yes |
| Whole body paralysis | No | Yes |

Neutralization of BoNT/A3 and BoNT/A1 using an anti-BoNT/A1 antibody: The neutralization results showed that 2 μl of anti-BoNT/A1 antibody was able to fully neutralize 10,000 $LD_{50}$ of BoNT/A1, but was not able to neutralize 15,000 $LD_{50}$. However, the same mount of anti-BoNT/A1 could only neutralize 1000 $LD_{50}$ of BoNT/A3, but not 2,500 $LD_{50}$ of BoNT/A3. It was determined that 2 μl of anti-BoNT/A1 can neutralize 12,245 $LD_{50}$ of BoNT/A1 vs. only 1,582 $LD_{50}$ of BoNT/A3 which was an ~8 fold difference. These data indicate that there may be important differences in epitopes between BoNT/A1 and BoNT/A3, leading to differences in neutralizing antibody formation in immunized animals.

We claim:

1. A method of treating a patient having a symptom in need of botulinum toxin therapy, wherein the patient is treated with an effective amount of a preparation of *Clostridium botulinum* neurotoxin BoNT/A3, wherein the preparation is at least 90% pure BoNT/A3, and wherein the patient produces neutralizing antibodies directed against BoNT/A1 during or following treatment of the patient using a BoNT/A1 neurotoxin or BoNT/A1 neurotoxin complex.

2. The method of claim 1, wherein the treatment is for a condition selected from the group consisting of cervical dystonia, blepharospasm, severe primary axillary hyperhidrosis, strabismus, achalasia, chronic focal neuropathies, migraine, other headache disorders, cosmetic issues, muscle spasms, upper motor neuron syndrome, and sweating.

3. The method of claim 1, wherein treatment comprises administration of pure BoNT/A1 neurotoxin or pure BoNT/A1 neurotoxin complex.

4. The method of claim 1, wherein specific toxicity of the preparation is at least $5\times10^7$ $LD_{50}$ per m/g.

* * * * *

UNITED STATES PATENT AND TRADEMARK OFFICE
CERTIFICATE OF CORRECTION

Page 1 of 1

PATENT NO. : 9,498,521 B2
APPLICATION NO. : 13/627540
DATED : November 22, 2016
INVENTOR(S) : Johnson et al.

It is certified that error appears in the above-identified patent and that said Letters Patent is hereby corrected as shown below:

In the Claims

Column 10, Line 43 - "m/g" should be -- mg --

Signed and Sealed this
Sixth Day of March, 2018

Andrei Iancu
*Director of the United States Patent and Trademark Office*